(12) United States Patent
Booth et al.

(10) Patent No.: US 7,871,410 B2
(45) Date of Patent: Jan. 18, 2011

(54) SYSTEM FOR, AND METHOD OF, HEATING A BIOLOGICAL SITE IN A PATIENT'S BODY

(75) Inventors: Norman Booth, Wattle Grove (AU); Evan K. Chong, South Strathfield (AU)

(73) Assignee: CathRx Ltd, Homebush Bay, NSW (AU)

( * ) Notice: Subject to any disclaimer, the term of this patent is extended or adjusted under 35 U.S.C. 154(b) by 997 days.

(21) Appl. No.: 10/532,391

(22) PCT Filed: Oct. 28, 2003

(86) PCT No.: PCT/AU03/01421

§ 371 (c)(1),
(2), (4) Date: Apr. 21, 2005

(87) PCT Pub. No.: WO2004/039274

PCT Pub. Date: May 13, 2004

(65) Prior Publication Data

US 2005/0273091 A1      Dec. 8, 2005

(30) Foreign Application Priority Data

Oct. 29, 2002   (AU) .............................. 2002952318

(51) Int. Cl.
- *A61F 7/12* (2006.01)
- *A61B 18/04* (2006.01)
- *A61B 18/08* (2006.01)
- *A61B 18/14* (2006.01)

(52) U.S. Cl. .............................. 606/34; 607/96; 607/99; 607/102; 606/32; 606/35; 606/41

(58) Field of Classification Search ................... 607/96, 607/99, 102; 606/34, 41
See application file for complete search history.

(56) References Cited

U.S. PATENT DOCUMENTS 3,601,126 A * 8/1971 Estes .......................... 606/35

(Continued)

FOREIGN PATENT DOCUMENTS

EP    0 479 435 A2    4/1992

(Continued)

OTHER PUBLICATIONS

International Search Report mailed on Feb. 2, 2004 for PCT patent application No. PCT/AU2003/001421 filed on Oct. 28, 2003, 7 pages.

(Continued)

*Primary Examiner*—Roy D Gibson
*Assistant Examiner*—Kaitlyn E Helling
(74) *Attorney, Agent, or Firm*—Morrison & Foerster LLP

(57) ABSTRACT

A system (10) for heating a biological site in a patient's body includes a transformer (14) having a primary winding and a secondary winding. The secondary winding has a tap (24) to provide a ground reference and two sources of radio frequency (RF) energy. An active electrode (16) is connected to each source to apply energy from its associated source to the site, the energy applied by one electrode (16) being out of phase with the energy applied by the other electrode (16).

22 Claims, 3 Drawing Sheets

U.S. PATENT DOCUMENTS

| | | | | |
|---|---|---|---|---|
| 3,730,188 A | | 5/1973 | Ellman | |
| 3,913,583 A | * | 10/1975 | Bross | 606/35 |
| 4,101,984 A | | 7/1978 | MacGregor et al. | |
| 4,200,105 A | * | 4/1980 | Gonser | 606/35 |
| 4,520,818 A | * | 6/1985 | Mickiewicz | 606/40 |
| 4,531,524 A | * | 7/1985 | Mioduski | 607/99 |
| 4,871,421 A | * | 10/1989 | Ogle et al. | 438/710 |
| 5,269,810 A | | 12/1993 | Hull et al. | |
| 5,300,068 A | * | 4/1994 | Rosar et al. | 606/34 |
| 5,383,917 A | | 1/1995 | Desai et al. | |
| 5,431,649 A | * | 7/1995 | Mulier et al. | 606/41 |
| 5,507,743 A | * | 4/1996 | Edwards et al. | 606/41 |
| 5,522,874 A | | 6/1996 | Gates | |
| 5,540,684 A | * | 7/1996 | Hassler, Jr. | 606/40 |
| 5,615,091 A | * | 3/1997 | Palatnik | 363/17 |
| 5,620,481 A | | 4/1997 | Desai et al. | |
| 5,693,078 A | | 12/1997 | Desai et al. | |
| 5,697,928 A | | 12/1997 | Walcott et al. | |
| 5,834,051 A | | 11/1998 | Woloszko et al. | |
| 5,892,667 A | | 4/1999 | Glasband et al. | |
| 5,931,862 A | | 8/1999 | Carson | |
| 6,071,278 A | | 6/2000 | Panescu et al. | |
| 6,112,123 A | * | 8/2000 | Kelleher et al. | 607/98 |
| 6,267,757 B1 | * | 7/2001 | Aita et al. | 606/33 |
| 6,280,441 B1 | * | 8/2001 | Ryan | 606/45 |
| 6,485,487 B1 | * | 11/2002 | Sherman | 606/34 |
| 6,508,815 B1 | * | 1/2003 | Strul et al. | 606/34 |
| 7,178,234 B2 | | 2/2007 | Kawasaki et al. | |
| 2001/0014804 A1 | * | 8/2001 | Goble et al. | 606/41 |
| 2003/0199868 A1 | | 10/2003 | Desai et al. | |

FOREIGN PATENT DOCUMENTS

| | | |
|---|---|---|
| EP | 0 479 435 A3 | 4/1992 |
| JP | 08-000635 A | 1/1996 |
| WO | WO-90/08466 A1 | 8/1990 |
| WO | WO-95/25472 A1 | 9/1995 |
| WO | WO-96/36860 A2 | 11/1996 |
| WO | WO-96/36860 A3 | 11/1996 |
| WO | WO-96/37156 A1 | 11/1996 |
| WO | WO-99/58070 A2 | 11/1999 |
| WO | WO-02/080792 A1 | 10/2002 |
| WO | WO-2004/039274 A1 | 5/2004 |

OTHER PUBLICATIONS

Supplementary Partial European Search Report mailed Feb. 12, 2007 for EP Application No. 01977995.8, five pages.

Supplementary Partial European Search Report mailed Feb. 20, 2006, for EP Patent Application No. 03769029.4, filed Oct. 28, 2003, 7 pages.

* cited by examiner

TIME

— SINGLE ELECTRODE
— COMP. ELECTRODE 1
— COMP. ELECTRODE 2
— VOLTAGE BETWEEN COMP. ELECTRODES

SYSTEM FOR, AND METHOD OF, HEATING A BIOLOGICAL SITE IN A PATIENT'S BODY

FIELD OF THE INVENTION

This invention relates to the heat treatment of a biological site in a human or animal body. More particularly, the invention relates to a system for, and method of, heating a biological site in a patient's body to produce at least one lesion at the site or for the treatment of pain management and to a component for use in the system.

BACKGROUND TO THE INVENTION

Electromagnetic energy, in the form of radio frequency (RF) energy, is frequently used to produce lesions at a biological site in the human or animal body for many purposes such as, for example, for cardiac ablation purposes, for tumour ablation, etc. RF energy can also be used for heating a site for the treatment of pain management. To apply the RF energy at the required site in the body, an electrode is used as a conductor with an electrode tip forming a first terminal of the circuit and a backplate beneath the patient's body forming a ground electrode for the circuit so that, when the electrode tip is brought into contact with the site, a closed circuit is formed. A problem with this arrangement is that the impedance of the patient's body is high resulting in dissipation of the RF energy through the patient's body rather than being concentrated at the site.

Traditionally lesions have been produced at a site using a single active electrode system. The RF energy is applied to a small electrode tip towards the end of a catheter with an earth connection being made via the patient's body.

SUMMARY OF THE INVENTION

According to a first aspect of the invention, there is provided a system for heating a biological site in a patient's body, the system including:

a transformer having a primary winding and a secondary winding, the secondary winding having at least one tap to provide a ground reference and at least two sources of radio frequency (RF) energy; and at least one active electrode connected to each source to apply energy from its associated source to the site, the energy applied by the at least one electrode of any one of the sources being out of phase with the energy applied by the at least one electrode of any of the other sources.

The system may include an energy generator for generating the RF energy, the primary winding of the transformer being connected to an output of the energy generator. Instead, an impedance matching network may be used to facilitate use of existing equipment.

A reference, or indifferent, electrode may be connected to the at least one tap.

The transformer may have a 1:1 ratio between the primary winding and the secondary winding. Preferably, the tap is a centre tap to provide two sub-windings which act as energy sources with the energy supplied by the sources being 180° out of phase with respect to each other, but of equal amplitude, so that the total energy applied to the site is equivalent to the energy applied by a single electrode system.

At least one active electrode may be connected to a free end of each sub-winding opposite the end of the sub-winding connected to the tap.

Further, the system may use more than two electrodes. Then, a plurality of electrodes may be connected to the free end of each sub-winding, the electrodes of the sub-windings being arranged in groups relative to the site so that energy is applied across the site to effect heating of the site to produce a lesion or for pain management.

In addition, or instead, the secondary winding may have at least one intermediate tap between the ground reference tap and the free end of each sub-winding to provide more than two sub-windings acting as energy sources. At least one active electrode may be connected to each intermediate tap, the positions of the intermediate taps being selected to maintain sufficient potential difference between adjacent electrodes at the site, in use, to produce longer lesions.

While the system has been designed specifically for heating the site to an extent sufficient to cause the production of lesions in the heart for treatment of atrial fibrillation, the system may equally well be used for treatments of other forms of arrhythmia, for example, ventricular tachycardia. The electrodes may therefore be arranged transmurally, i.e. through a ventricular wall of the heart, for producing a transmural lesion at the relevant site to treat ventricular tachycardia. The system is also able to be used in the treatment of pain management where the site is heated to a temperature to ease discomfort caused by pain but insufficient to cause the production of lesions.

To facilitate mounting of the electrodes at the relevant site, in particular, in treating ventricular tachycardia, the at least one active electrode may be an electrode assembly comprising a co-axially arranged pair of electrodes, the electrodes of the assembly being displaceably arranged relative to each other. At least one of the electrodes may have a helical tip to be screwed into the site.

As a development of this arrangement, both electrodes of the assembly may be helical-tipped to be screwed into the site. The helical-tipped electrodes may be of different pitches so that the depth into the site to which the electrodes extend, in use, differ with respect to each other.

According to a second aspect of the invention, there is provided a method of heating a biological site in a patient's body the method including the steps of:

providing a transformer having a primary winding and a secondary winding, the secondary winding having at least one tap to provide a ground electrode and at least two sources of RF energy;

connecting at least one active electrode to each source; and attaching the at least one active electrode from each source to the site and applying the energy from the sources to the site, the energy applied by the at least one electrode of any one of the sources being out of phase with the energy applied by the at least one electrode of any of the other sources.

The method may include providing an energy generator for generating the RF energy and connecting the primary winding of the transformer to an output of the generator. The transformer may be connected to the energy generator via an impedance matching network to facilitate use of existing equipment.

The method may include connecting a reference electrode to the at least one tap.

Further, the method may include selecting the transformer to have a 1:1 ratio between the primary winding and the secondary winding. The method may include centre-tapping the transformer to provide two sub-windings which act as energy sources with the energy supplied by the sources being 180° out of phase, but of equal amplitude, with respect to each other.

The method may include connecting at least one active electrode to a free end of each sub-winding opposite the end of the sub-windings connected to the tap. In addition, or instead, the method may include connecting a plurality of electrodes to the free end of each sub-winding and arranging the electrodes in groups relative to the site. Also, in addition, or instead, the method may include forming at least one intermediate tap between the ground reference tap and the free end of each sub-winding to provide more than two sub-windings acting as energy sources and connecting at least one active electrode to each intermediate tap, the positions of the intermediate taps being selected to maintain sufficient potential difference between adjacent electrodes at the site, in use, to produce longer lesions.

Still further, the method may include arranging the electrodes transmurally at the site for the treatment of particular forms of arrhythmia, eg, ventricular tachycardia. With this arrangement a transmural lesion is produced at the relevant site.

The method may include arranging the at least one active electrode as a co-axially arranged pair of electrodes, the electrodes of the pair being displaceably arranged relative to each other. The method may include providing at least one of the co-axially arranged pair of electrodes with a helical tip. Both electrodes of the co-axially arranged pair of electrodes may be helical-tipped and the method may include screwing the electrodes into the site to different depths to heat the site to the required depth. To facilitate this, the tips may be of different pitches.

The invention extends also to a component for use in heating a biological site in a patient's body, the component including a pair of co-axially arranged electrodes, at least one of which has a helical tip.

Preferably, both electrodes have helical tips. A pitch of one tip may differ with respect to a pitch of the other tip.

BRIEF DESCRIPTION OF THE DRAWINGS

The invention is now described by way of example with reference to the accompanying drawings in which.

DETAILED DESCRIPTION OF THE DRAWINGS

Figure 1:
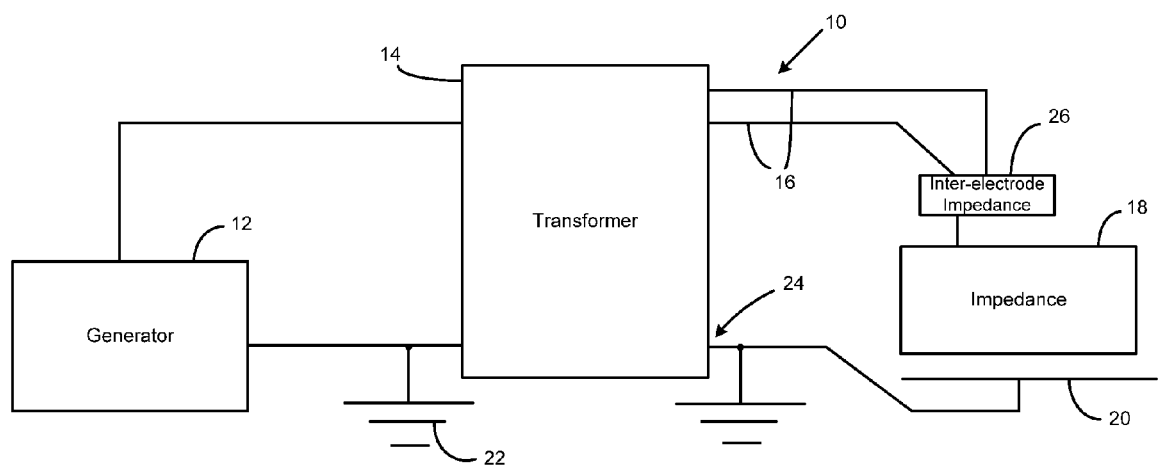
FIG. 1 shows a block diagram of a system, in accordance with an embodiment of the invention, for heating a biological site in a patient's body.

Referring initially to FIG. 1 of the drawings, a system, in accordance with an embodiment of the invention, for heating a biological site in a patient's body is illustrated and is designated generally by the reference numeral 10. The system 10 comprises a generator 12 for generating electromagnetic energy, more particularly, radiofrequency (RF) energy.

A transformer 14 is connected to an output of the RF generator 12. At least two active electrodes 16 are connected to outputs of the transformer 14, as will be described in greater detail below. By "active" is meant that, unless the context clearly indicates otherwise, the electrode is used to impart energy to the site.

The system 10 makes use of a patient's body as an impedance 18 and a closed circuit is formed by the use of a reference, or indifferent, electrode 20. The reference electrode 20 is tied to a ground 22 of the RF generator 12.

The transformer 14 is a centre-tapped transformer, a secondary winding of the transformer 14 having a centre tap 24 to form two separate sub-windings. The reference electrode 20 is connected to the centre tap 24. One of the active electrodes 16 is connected to an opposed, or free, end of each of the sub-windings of the transformer 14 formed by the centre tapping of the secondary winding. The transformer 14 may, optionally have intermediate taps (not shown) formed between the centre tap and each free end of each sub-winding. In that case, at least one active electrode may be connected to adjacent intermediate taps. The positions of the intermediate taps are selected to maintain sufficient potential difference between adjacent electrodes at the site to produce longer lesions.

The transformer 14 makes use of a 1:1 ratio between its primary winding and the secondary winding. Different ratios may be employed bearing in mind that, if a number of turns of the windings of the secondary winding are increased relative to that of the primary winding, the voltage across each secondary winding will increase with a corresponding decrease in current.

In addition, the materials used in the transformer 14 are selected to be capable of withstanding energy levels and frequencies involved in ablative therapies. The transformer 14 and the materials used are optimised to ensure maximum transfer of energy to the active electrodes 16.

Thus, suitable materials for the transformer 14 include nickel-zinc or manganese-zinc ferrites for a core of the transformer 14, in particular F8, F12, F14 ferrites. These materials are able to operate at the required frequencies and have the necessary high initial permeability and high saturation flux. It will be appreciated that dimensions of the core, number of turns of the windings and the diameter used for the windings are selected so that the transformer 14 has low insertion losses to ensure efficient transfer of energy.

The primary winding of the transformer 14 matches the output impendence of the generator. The generator 12 used in trials had an output impedance of between about 30 and 300 ohms. A series resistor and/or a parallel capacitor may be required to effect impedance matching.

The system 10 is designed particularly for use in the production of lesions at a site in a patient's body for treating various disorders such as atrial fibrillation, ventricular tachycardia, tumour ablation, pain management, etc. Traditionally, systems for treatment of these disorders have used a single electrode with a backplate under the patient's body forming a return connection. This results in a large percentage of energy dissipation through the patient's body rather than being used for ablative purposes at the site in the patient's body.

With the provision of two active electrodes 16 in the system 10 of the present invention, an inter-electrode impedance, illustrated schematically at 26, is created between the active electrodes 16 resulting in greater energy transfer between the electrodes 16 rather than through the patient's body.

Figure 2:
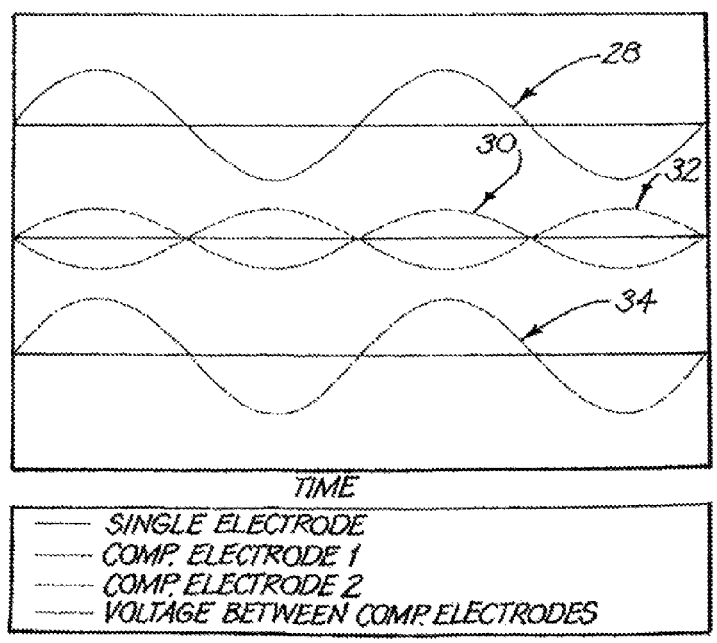
FIG. 2 shows a graph of various comparative waveforms.

A representation of this is shown in FIG. 2 of the drawings where waveform 28 is the voltage waveform of a single electrode of a prior art system. Voltage waveforms 30 and 32 are the 180° out of phase waveforms of each active electrode 16 of the system 10 of the present invention and waveform 34 is the sum of the absolute values of the amplitudes of the waveforms 30 and 32. Thus, it will be noted that the voltage between the electrodes 16, as represented by the waveform 34, is the same as the voltage of a single electrode 28 but that the energy is concentrated between the active electrodes 16 rather than between an electrode and any indifferent electrode relying on the patient's body.

It is to be noted that, in total, the energy of the system 10 is no higher than that of a prior art system as the energy applied to each active electrode 16 by the transformer 14 is half that applied to the single electrode of the prior art system.

The applicant believes that, with the concentration of energy between the active electrodes 16 of the present system 10, larger and deeper lesions may be formed between the two electrodes 16 than can be produced by a single electrode using the same RF energy. The reason for this is that the inter-electrode impedance 26 is much lower than that of the patient's body resulting in energy transfer between the electrodes 16 rather than dissipation of energy through the patient's body.

Table 1 below shows various tests which have been carried out experimentally.

TABLE 1

| No. | Notes | Spacing (mm) | Power (W) | Time (s) | Depth (mm) |
|---|---|---|---|---|---|
| 1 | 2cath 2 mm elect in phase | 0 | 20 | 120 | 4 |
| 2 | 2cath 2 mm elect out phase | 0 | 20 | 120 | 3.5 |
| 3 | 2cath 2 mm elect out phase | 2 | 20 | 120 | 3.5 |
| 4 | 2cath 2 mm elect out phase | 5 | 20 | 120 | 6 |
| 5 | 2cath 2 mm elect out phase | 6.5 | 20 | 120 | 4.5 |
| 6 | 2cath 2 mm elect out phase | 9 | 20 | 120 | 5 |
| 7 | 2cath 2 mm elect in phase (crossed) | 0 | 20 | 120 | No lesion |
| 8 | 2cath 2 mm elect in phase (crossed) | 0 | 20 | 120 | No lesion |
| 9 | 2cath 2 mm elect in phase | 0 | 20 | 120 | 4 |
| 10 | 1cath 2 mm | — | 20 | 120 | 4.5 |
| 11 | Three burn series (as 10) #1 | — | 20 | 120 | 5 |
| 12 | Three burn series (as 10) #2 | — | 20 | 120 | 5 |
| 13 | Three burn series (as 10) #3 | — | 20 | 120 | 5 |
| 14 | 2cath 2 mm elect in phase | 7 | 20 | 120 | 3.5 |
| 15 | 2cath pairs elect out phase (long elect) | 4 | 20 | 120 | 6 |
| 16 | 2cath 4 mm elect in phase | 0 | 20 | 120 | 0.5 |
| 17 | 2cath 4 mm elect out phase | 0 | 20 | 120 | 6 |
| 18 | 2cath 4 mm elect out phase | 4 | 20 | 120 | 6 |
| 19 | 2cath 4 mm elect out phase | 7 | 20 | 120 | 8 |
| 20 | 2cath 4 mm elect out phase | 11 | 20 | 120 | 8 |
| 21 | 2cath 4 mm elect in phase | 0 | 20 | 120 | 0.5 |
| 22 | 2cath 4 mm elect in phase | 6 | 20 | 120 | 0.5 |
| 23 | 1 cath 4 mm | — | 20 | 120 | 5 |
| 24 | 2cath 4 mm elect out phase transmural | — | 20 | 120 | 13 - high damage |
| 25 | 2cath 4 mm elect out phase | 4 | 10 | 120 | 5 |
| 26 | 2cath 4 mm elect out phase | 4 | 20 | 60 | 7 |
| 27 | 2cath 4 mm elect out phase | 4 | 20 | 30 | 5 |
| 28 | 2cath 4 mm elect in phase transmural | — | 20 | 120 | 6 - low damage |

A comparison between the various tests carried out shows that, with the provision of two electrodes relying on complementary and 180° out of phase energy, deeper lesions are formed. Reference is made particularly to tests 19 and 23 where it is to be noted that, with the use of the two active electrodes 16, a deeper lesion was formed than was the case with a single electrode.

Once again, comparing items 24 and 28, relating to transmural lesions, the use of the two out of phase electrodes 16 of the present system 10 (test 24) resulted in a significantly deeper lesion than using two electrodes in phase as shown by test 28.

To create a transmural lesion, particularly for the treatment of atrial fibrillation, one electrode may be placed thoroscopically through the chest with a second electrode being inserted via a catheter inside the heart to achieve lesions through the heart wall.

Another approach contemplated for use with the present system 10 is the use of a component 30 comprising two, co-axially arranged electrodes for the treatment of ventricular tachycardia. In the embodiment shown in FIG. 3 of the drawings, the component 30 includes an inner electrode 32 which is a retractable electrode inserted via a catheter 34. The inner electrode 32 is screwed into position in tissue 36 at the site to be treated by means of a screw driver stylet (not shown) inserted through a lumen of the catheter 34 to extend the screw tipped electrode 32 relative to an outer, second electrode 38 into the tissue 36 of the heart wall. The second electrode 38, which may be fixed or retractable, is placed in contact with the endocardium of the heart to effect the production of a transmural legion 40.

The actual length of exposed metal of the screw electrode 32 can be optimised by insulating a portion of the screw. For example, the screw tip may be 20 mm long but only the most distal 5 mm is exposed metal. It will also be appreciated that the actual depth to which the electrode 32 is screwed into the tissue 36 of the heart wall is variable depending on the treatment required.

It will also be appreciated that the two electrodes 32, 38 are insulated from each other.

Figure 3:
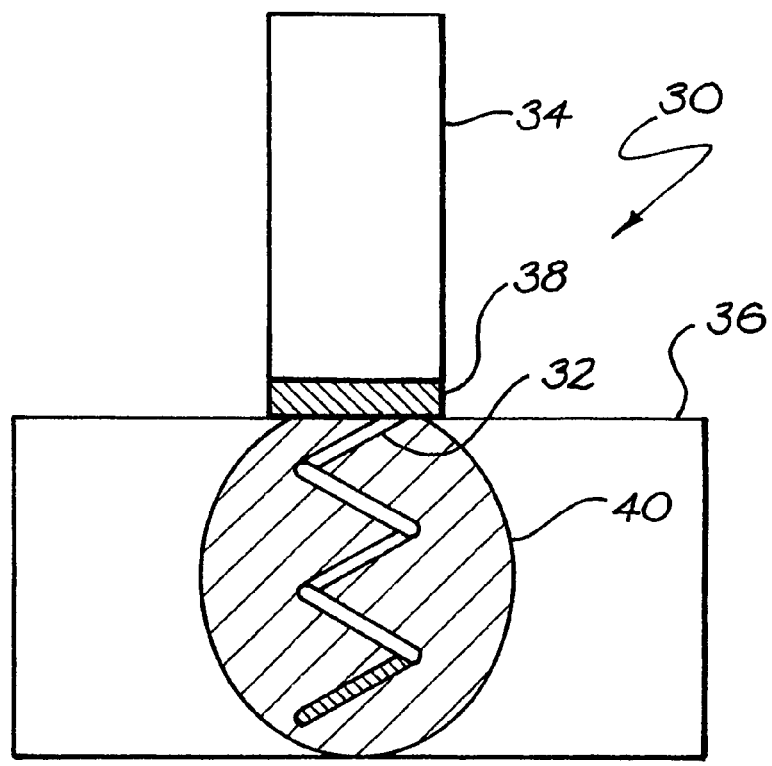
FIG. 3 shows a schematic representation of one embodiment of a component of the system of FIG. 1.
Figure 4:
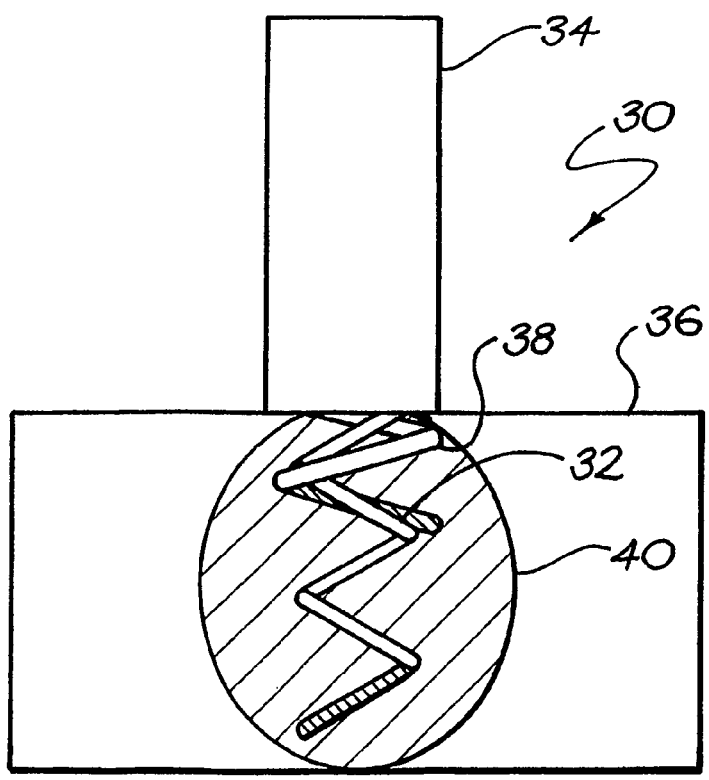
FIG. 4 shows a schematic representation of another embodiment of the component of the system of FIG. 1.

A variation of this arrangement is the use of two screw-tipped electrodes insulated from each other. This embodiment of the component is shown in FIG. 4 of the drawings. With reference to FIG. 3 of the drawings, like reference numerals refer to like parts unless otherwise specified.

In this embodiment, both electrodes 32 and 38 are screw-tipped or helical-tipped. The screw tip of the inner electrode 32 has a larger pitch than the outer electrode 38. Hence, when the electrodes 32, 38 are extended out of the catheter 34, the electrode 32 is screwed into the tissue 36 of the heart wall to a greater depth than the electrode 38. The finer pitched, outer electrode is urged into contact with the endocardium. Once again, screw depth can be optimised depending on the depth of the conductive fibres causing the arrhythmia.

The applicant is of the view that the use of concentric electrodes, in particular, would be useful for the treatment of ventricular tachycardia but could be of use in other applications as well.

Figure 5:
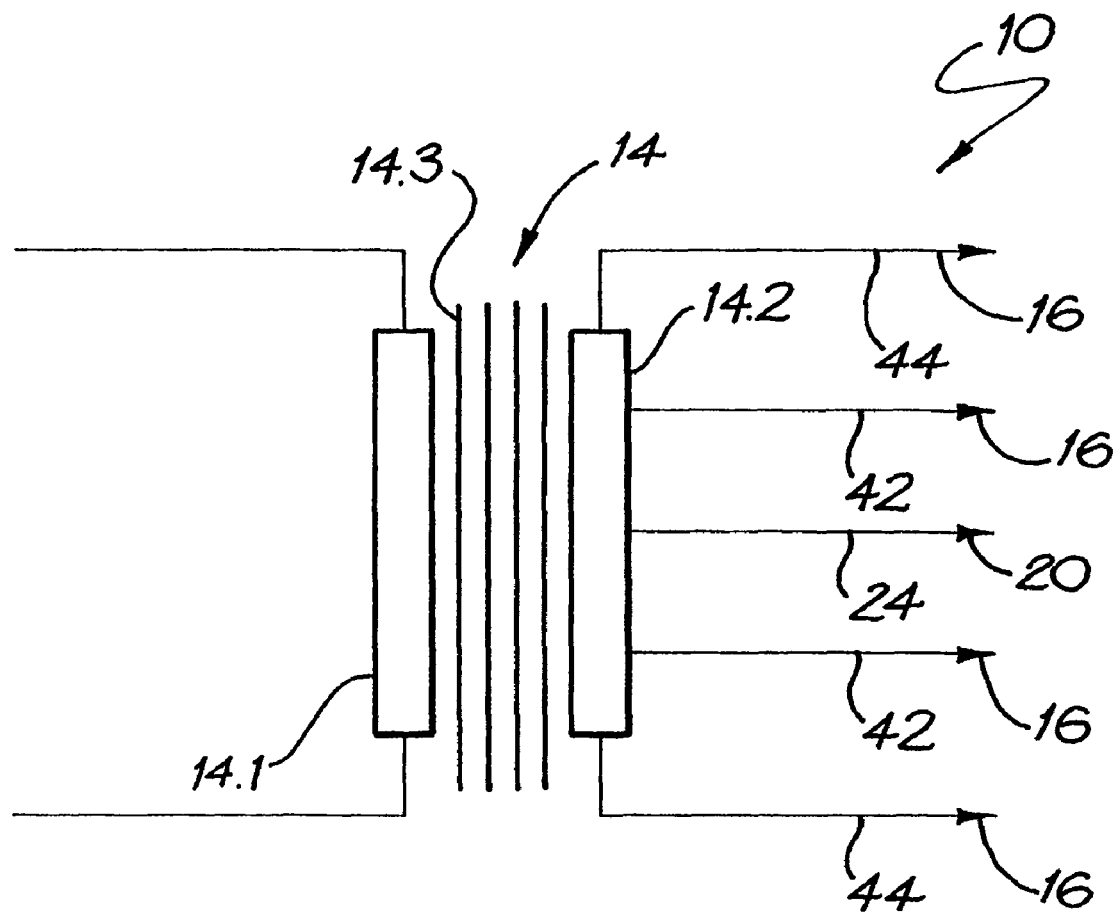
FIG. 5 shows a block diagram of a system, in accordance with a second embodiment of the invention, for heating a biological site in a patient's body.

In another embodiment of the invention, the transformer 14 of the system 10 has multiple taps in its secondary winding. This embodiment of the invention is illustrated schematically in FIG. 5 of the drawings. With reference to FIG. 1 of the drawings, like reference numerals refer to like parts, unless otherwise specified.

Hence, the transformer 14 has a primary winding 14.1 and a secondary winding 14.2 wound about a core 14.3. The core 14.3 is made from one of the materials referred to above. The secondary winding 14.3 has the centre tap 24 and an intermediate tap 42 connected between each end tap 44 and the centre tap 24.

An active electrode 16 is connected to each tap 42 and 44 and the ground electrode 20 is connected to the centre tap 24. The signals provided to each electrode 16 on the same side of the centre tap 24 are in phase but are at a predetermined potential difference relative to each other and to the centre tap 24. The value of this potential difference is governed by the number of turns of the secondary winding. The signals provided to the taps 42 and 44 and, hence, the electrodes 16 connected to those taps 42 and 44, on one side of the centre tap 24 are 180° out of phase with the signals provided to the taps 42 and 44 and, hence, their associated electrodes 16, on the other side of the centre tap.

With the provision of the intermediate taps 42, a greater surface area of the site can be heated. Hence, where the site is undergoing heating to create lesions, longer lesions are formed as a result of using the electrodes 16 connected to the intermediate taps 42 in addition to the electrodes 44 connected to the end taps 44.

Optimisation of the system 10 involves the positioning of the tap 24 on the secondary winding of the transformer 14 as well as the shape and size of the electrodes 16. To reduce charring at the site, the electrodes connected to the sub-windings of the secondary winding may be arranged in groups, for example, pairs. By placing the electrodes in groups, each electrode may impart lower energy to the site thereby reducing the likelihood of charring. In addition, use of multiple electrodes can be used for pain management with the RF energy being delivered through at least two of the electrodes simultaneously. The positioning of two electrodes may be less dangerous than a single electrode with an earth electrode. For example, in pain management where energy is applied to a patient's spine, placing an electrode on each side of the spine rather than one directly into the spine may be less risky. It will be appreciated that, for pain management, no ablating occurs and the electrodes are therefore operated at power levels insufficient to cause ablation of the tissue.

In addition, for ablating a tumour, by placing the electrodes 16 on opposite sides of the tumour, more mass of the tumour can be ablated than with the use of a single electrode.

Accordingly, it is an advantage of the invention that a system 10 and method are provided where, due to energy transfer between the active electrodes 16, deeper lesion production and more accurate lesion production is facilitated. In addition, the use of a pair of active electrodes reduces the risks involved in the production of lesions for treatment of various disorders.

The use of at least two active electrodes is of significant benefit in creating linear lesions such as used in "Maze-like" procedures as well as in the production of transmural lesions which are beneficial in treating ventricular tachycardia.

Another major benefit of the system 10 is the use of a centre-tapped transformer to provide the out of phase energy sources. The centre tapped transformer considerably reduces the complexity of the system 10 as the need for complicated and expensive control circuitry is obviated. The transformer 14 provides the energy sources in a simple but reliable way. The use of the transformer 14 also obviates the need for complex set-up procedures. In effect, the transformer 14 need only be connected to the generator 12, the electrodes 16 positioned and the system 10 is ready for use. No complicated calibration or training procedures are required to use the system 10.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A system for heating a biological site in a patient's body, the system including:
   a transformer having a primary winding, a secondary winding and a ferrite core, the secondary winding having at least one tap to provide a ground reference and at least two sources of radio frequency (RF) energy;
   at least one active electrode connected to each source to apply energy from its associated source to the site, the energy applied by the at least one electrode of any one of the sources being out of phase with the energy applied by the at least one electrode of any of the other sources; and
   an indifferent electrode, in the form of a backplate, connected to the ground reference of the tap with the ground reference of the tap and the indifferent electrode being tied to a ground reference on the primary side of the transformer.

2. The system of claim 1 which includes an energy generator for generating the RF energy, the primary winding of the transformer being connected to an output of the energy generator.

3. The system of claim 1 in which the transformer has a 1:1 ratio between the primary winding and the secondary winding.

4. The system of claim 1 in which the tap is a centre tap to provide two sub-windings which act as energy sources with the energy supplied by the sources being 180° out of phase with respect to each other.

5. The system of claim 4 in which at least one active electrode is connected to a free end of each sub-winding opposite the end of the sub-winding connected to the tap.

6. The system of claim 5 in which a plurality of electrodes are connected to the free end of each sub-winding, the electrodes being arranged in groups relative to the site.

7. The system of claim 5 in which the secondary winding has at least one intermediate tap between the ground reference tap and the free end of each sub-winding to provide more than two sub-windings acting as energy sources with at least one active electrode being connected to each intermediate tap.

8. The system of claim 1 in which the at least one active electrode is an electrode assembly comprising a co-axially arranged pair of electrodes, the electrodes of the assembly being displaceably arranged relative to each other.

9. The system of claim 8 in which at least one of the electrodes has a helical tip to be screwed into the site.

10. The system of claim 9 in which both electrodes of the assembly are helical-tipped to be screwed into the site.

11. The system of claim 10 in which the helical-tipped electrodes are of different pitches so that the depth into the site to which the electrodes extend, in use, differ with respect to each other.

12. A method of heating a biological site in a patient's body the method including the steps of:
   providing a transformer having a primary winding, a secondary winding and a ferrite core, the secondary winding having at least one tap to provide a ground reference and at least two sources of RF energy and an indifferent electrode, in the form of a backplate, connected to the ground reference of the tap with the ground reference of the tap and the indifferent electrode being tied to a ground reference on a primary side of the transformer;
   connecting at least one active electrode to each source; and
   attaching the at least one active electrode from each source to the site and applying the energy from the sources to the site, the energy applied by the at least one electrode of any one of the sources being out of phase with the energy applied by the at least one electrode of any of the other sources.

13. The method of claim 12 which includes providing an energy generator for generating the RF energy and connecting the primary winding of the transformer to an output of the generator.

14. The method of claim 12 which includes selecting the transformer to have a 1:1 ratio between the primary winding and the secondary winding.

15. The method of claim 12 which includes centre-tapping the transformer to provide two sub-windings which act as energy sources with the energy supplied by the sources being 180° out of phase with respect to each other.

16. The method of claim 15 which includes connecting at least one active electrode to a free end of each sub-winding opposite the end of the sub-winding connected to the tap.

17. The method of claim 16 which includes connecting a plurality of electrodes to the free end of each sub-winding and arranging the electrodes in groups relative to the site.

18. The method of claim 16 which includes forming at least one intermediate tap between the ground reference tap and the free end of each sub-winding to provide more than two sub-windings acting as energy sources and connecting at least one active electrode to each intermediate tap.

19. The method of claim 16 which includes arranging the electrodes transmurally at the site.

20. The method of claim 16 which includes arranging the at least one active electrode as a co-axially arranged pair of electrodes, the electrodes of the pair being displaceably arranged relative to each other.

21. The method of claim 20 which includes providing at least one of the co-axially arranged pair of electrodes with a helical tip.

22. The method of claim 21 in which both electrodes of the co-axially arranged pair of electrodes are helical-tipped and in which the method includes screwing the electrodes into the site to different depths to heat the site to the required depth.

* * * * *